(12) United States Patent
Tenorio et al.

(10) Patent No.: US 8,956,493 B2
(45) Date of Patent: Feb. 17, 2015

(54) LEG AND FLAP ELASTIC COMPOSITE FOR AN ABSORBENT ARTICLE AND METHOD OF MANUFACTURING SAME

(75) Inventors: Luis Alberto Tenorio, Menasha, WI (US); Jeffrey Alan DeBroux, Appleton, WI (US); David Kyle Stankewicz, Appleton, WI (US); Darin Allen Engelhart, Appleton, WI (US); James Richard Schermerhorn, Neenah, WI (US); Michael Donald Sperl, Waupaca, WI (US); Daniel Mark Duhm, Greenville, WI (US); Michael Lee Lohoff, Oshkosh, WI (US); Anita Marie-Nanette Gilgenbach, Neenah, WI (US); Kenneth James Quella, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 535 days.

(21) Appl. No.: 12/971,896

(22) Filed: Dec. 17, 2010

(65) Prior Publication Data
US 2012/0157958 A1 Jun. 21, 2012

(51) Int. Cl.
*B32B 38/04* (2006.01)
*B32B 38/10* (2006.01)
*A61F 13/15* (2006.01)
(Continued)

(52) U.S. Cl.
CPC ..... *A61F 13/15593* (2013.01); *A61F 13/15756* (2013.01); *A61F 13/4753* (2013.01); *A61F 13/49015* (2013.01); *A61F 13/49017* (2013.01); *A61F 2013/49036* (2013.01)

USPC ........... 156/257; 156/252; 156/253; 156/256; 156/259; 156/268; 156/269

(58) Field of Classification Search
CPC .............. A61F 13/49; A61F 13/49015; A61F 13/49017; A61F 13/4753; B32B 38/00; B32B 38/04; B32B 38/004
USPC ......... 156/250, 252, 253, 256, 257, 259, 268, 156/269; 604/385.21, 385.24, 385.25
See application file for complete search history.

(56) References Cited

U.S. PATENT DOCUMENTS 4,041,203 A 8/1977 Brock et al.
4,081,301 A 3/1978 Buell
(Continued)

FOREIGN PATENT DOCUMENTS

EP 0217032 4/1987
EP 0556749 A1 8/1993
(Continued)

OTHER PUBLICATIONS

International Search Report and Written Opinion for PCT/IB2011/055058 dated Jul. 31, 2012; 9 pages.

*Primary Examiner* — Mark A Osele
*Assistant Examiner* — Christopher C Caillouet
(74) *Attorney, Agent, or Firm* — Armstrong Teasdale LLP

(57) ABSTRACT

A method of manufacturing a leg and flap elastics composite for use in an absorbent article includes joining a leg elastic member to a web moving in a machine direction. A flap elastic member is joined to the web and spaced from the leg elastic member. The web is fed to a chopper assembly wherein portions of the leg and flap elastic members are rendered less elastic at spaced-apart intervals to define deadened portions of the leg and flap elastic members.

28 Claims, 8 Drawing Sheets

(51) Int. Cl.
*A61F 13/475* (2006.01)
*A61F 13/49* (2006.01)

(56) References Cited

U.S. PATENT DOCUMENTS

| | | | |
|---|---|---|---|
| 4,515,595 A | 5/1985 | Kievit | |
| 4,663,220 A | 5/1987 | Wisneski | |
| 4,846,825 A * | 7/1989 | Enloe et al. | 604/385.22 |
| 4,940,464 A | 7/1990 | Van Gompel | |
| 5,046,272 A | 9/1991 | Vogt et al. | |
| 5,104,116 A | 4/1992 | Pohjola | |
| 5,224,405 A | 7/1993 | Pohjola | |
| 5,226,992 A | 7/1993 | Morman | |
| 5,486,166 A | 1/1996 | Bishop et al. | |
| 5,490,846 A | 2/1996 | Ellis et al. | |
| 5,643,243 A * | 7/1997 | Klemp | 604/385.28 |
| 5,820,973 A | 10/1998 | Dodge, II et al. | |
| 5,904,675 A | 5/1999 | Laux | |
| 5,911,713 A | 6/1999 | Yamada | |
| 5,931,825 A | 8/1999 | Kuen | |
| 5,993,433 A | 11/1999 | St. Louis | |
| 6,235,137 B1 | 5/2001 | Van Eperen et al. | |
| 6,248,097 B1 | 6/2001 | Beitz | |
| 6,465,073 B1 | 10/2002 | Morman | |
| 7,118,558 B2 * | 10/2006 | Wu et al. | 604/385.29 |
| 7,879,017 B1 * | 2/2011 | Tabata et al. | 604/385.23 |
| 2003/0105446 A1 | 6/2003 | Hutson et al. | |
| 2003/0114826 A1 * | 6/2003 | Roessler et al. | 604/385.28 |
| 2003/0226634 A1 | 12/2003 | Gardner, Jr. | |
| 2004/0044323 A1 | 3/2004 | Roessler et al. | |
| 2009/0324905 A1 * | 12/2009 | Welch et al. | 428/198 |

FOREIGN PATENT DOCUMENTS

| | | |
|---|---|---|
| EP | 1746960 B1 | 9/2009 |
| JP | 11244326 A | 9/1999 |
| JP | 2000079141 A | 3/2000 |
| WO | 9418927 A1 | 9/1994 |
| WO | 9605792 A1 | 2/1996 |
| WO | 9720532 A1 | 6/1997 |
| WO | 2005037160 A1 | 4/2005 |

* cited by examiner

LEG AND FLAP ELASTIC COMPOSITE FOR AN ABSORBENT ARTICLE AND METHOD OF MANUFACTURING SAME

BACKGROUND

The field of the invention relates generally to methods of manufacturing disposable absorbent articles and, more particularly, to methods of manufacturing leg and flap elastic composites for use in absorbent articles and absorbent articles having the leg and flap elastic composites.

Exemplary disposable absorbent articles include training pants, diapers, incontinence products, disposable underwear, medical garments, absorbent swim wear, and the like. Training pants (albeit, not exclusively) are disposable absorbent articles for use in the toilet training process. Toilet training is a process that includes many training techniques and aids that can be used by parents or other caregivers. One aspect of the total toilet training process is changing from the use of diapers to the use of training pants to help the child understand that he or she should now use the toilet.

Many caregivers underestimate the difficulty of teaching the toilet training process to young children. If a child does not respond to an initial toilet training instruction or introduction, the caregiver can be at a loss for finding techniques, methods, or teaching tools to encourage the child to master the art of toilet training. Thus, while various teaching tools such as books, videotapes, charts with stickers, personalized toilets, and interactive toilet training kits are available, there remains a need for improved motivational mechanisms to facilitate the toilet training process.

One motivational mechanism is the use of training pants having an improved aesthetic appearance. Specifically, a child is encouraged to wear a garment that resembles underwear worn by older children. Thus, there is an ongoing need to increase the appeal of the toilet training process to children, and to improve the aesthetic appearance of training pants. However, it is important that any modifications to the training pants to meet these needs do not compromise the use of the articles or any functional features of the articles (e.g., wetness indicators).

Current training pants typically include a waistband material that is adhesively applied to the pants and pressure bonded at its lateral edges to ensure secure attachment. After the waistband material is bonded to the pants, it is retracted to form a gather waistband of the respective pant. The resulting gathers, however, are often irregular. Additionally, the bond pattern at the edges of the waistband provides sufficient attachment but does not contribute to the aesthetics of the pants. In fact, the irregularities in the gathers of the waistband detract from the aesthetic appearance of many known training pants.

Often the waistband bond pattern of known training pants terminates before the lateral edges of the waistband material. Thus, occasionally the lateral edges of the waistband curl, expose underlying adhesive, and/or cause the training pants to stick together. These issues can create a negative impression in the consumer's mind of the product quality, and in some cases result in tearing of training pants.

Thus, it is desirable to provide a training pant having a uniformly gathered waistband, a waistband that is bonded at its lateral edges, and a waistband that does not curl.

Training pants typically include an outer cover, a body-side liner, an absorbent assembly disposed between the outer cover and the body-side liner, leg elastics, and flap (or barrier) elastics. The leg elastics are often disposed between the outer cover and the liner and adjacent the longitudinal side edges of the absorbent assembly. As a result, the spacing in the training pants suitable for placement of the leg elastics is very narrow, which limits the ability of the leg elastics to form an effective gasket with the leg since the absorbent assembly tends to pull the elastics away from the body when it is loaded with urine.

In current training pants, the leg elastics hold the absorbent assembly in place by gathering the crotch and enabling the flap elastics to make contact and form a gasket with the body of the wearer. This limits the effective MD length of the leg elastics in that the operative portions of the elastics cannot significantly overlap side panels of the training pants because doing so would put significant stress on the waistband and cause the training pant to droop.

Moreover, placing the leg elastics adjacent to the absorbent assembly and between the outer cover and body-side liner does not allow for elastic members to gather at the leg. Rather, this configuration creates a ruffle at the leg which makes the training pant appear more diaper-like.

There is a desire, therefore, to provide a training pant that enables an effective gasket to be formed by the leg elastics with the legs of the wearer. It is also desirable to provide a training pant that allows for a longer effective length of the leg elastics to thereby, in combination with the side panels, creates a fully encircling leg gasket. It is further desirable to provide a training pant having a more cuff-like appearance at each of the leg openings.

Furthermore, placing the leg elastics between the outer cover and body-side liner next to the absorbent assembly, as is often done in conventional training pants, limits the ability to use shaped absorbent assemblies since the absorbent assembly could interfere with the leg elastics. Shaped absorbent assemblies, however, can provide improved fit and exudates containment to the training pants.

Accordingly, it would be desirous to provide a training pant wherein the leg elastics did not inhibit the use of a shaped absorbent assembly.

Current training pant manufacturing techniques do not allow for a waistband bond pattern that covers the entire area of the waistband material because both the leg elastics and the flap elastics are "live" in the process until after the final cut-off. Pressure bonding a pattern over the entire waistband surface area would thus tie up the leg elastics and/or the flap elastics in the bonds, which would create live elastics running the entire length of the training pant. Such a design would cause fit problems, red marking, and process issues during folding and packaging. Moreover, the final cut-off during the manufacturing of the conventional training pants creates "tunnels" where the elastics existed prior to severing but retracted as a result of the severing. The "tunnels" are often susceptible to leakage.

Accordingly, a training pant manufacturing technique that enables a waistband bond pattern to be applied across the entire area of the waistband material and that eliminates the formation of "tunnels" is desirable.

In addition, current training pant manufacturing techniques often incorporate the use of a flap tackdown adhesive to ensure that the ends of the flap elastics are sealed to the product, which facilitates the formation of a containment bucket when the training pant is loaded with exudates. Currently, the application of the flap tackdown adhesive is not consistent, which results in the adhesive sometimes having a longer than desired tackdown length. The longer than desired tackdown length can significantly reduce the volume of the containment bucket.

As a result, it would be desirable to provide a training pant manufacturing technique that eliminate the use of flap tackdown adhesive altogether.

Moreover, current training pants typically include graphics in the leg and waist areas in order to provide the perception of encircling gaskets within these areas. Thus, it is also desirable to provide a training pant having leg elastics that extend beyond the outer cover thereby allowing the graphics to create a more noticeable encircling leg band.

BRIEF DESCRIPTION

In one aspect, a method of manufacturing a leg and flap elastics composite for use in an absorbent article generally comprises joining a leg elastic member to a web moving in a machine direction. A flap elastic member is joined to the web. The flap elastic member is spaced from the leg elastic member. The web is fed to a chopper assembly wherein portions of the leg and flap elastic members are rendered less elastic at spaced-apart intervals to define deadened portions of the leg and flap elastic members.

In another aspect, a method of manufacturing a liner/composite web generally comprises joining a leg elastic member to a web moving in a machine direction. A flap elastic member is joined to the web. The flap elastic member is spaced from the leg elastic member. The web is fed to a chopper assembly wherein portions of the leg and flap elastic members are rendered less elastic at spaced-apart intervals to define deadened portions of the leg and flap elastic members. The web is joined to a substrate adjacent at least one edge of the substrate after the web has been fed through the chopper assembly.

In yet another aspect, a method of manufacturing an absorbent article generally comprises joining a leg elastic member to a web moving in a machine direction. A flap elastic member is joined to the web. The flap elastic member is spaced from the leg elastic member. The web is fed to a chopper assembly wherein portions of the leg and flap elastic members are rendered less elastic at spaced-apart intervals to define deadened portions of the leg and flap elastic members. The web is joined to a substrate adjacent at least one edge of the substrate after the web has been fed through the chopper assembly. A plurality of absorbent assemblies is attached to the substrate. The substrate is cut into a plurality of discrete absorbent articles.

DETAILED DESCRIPTION OF THE DRAWINGS

Figure 1:
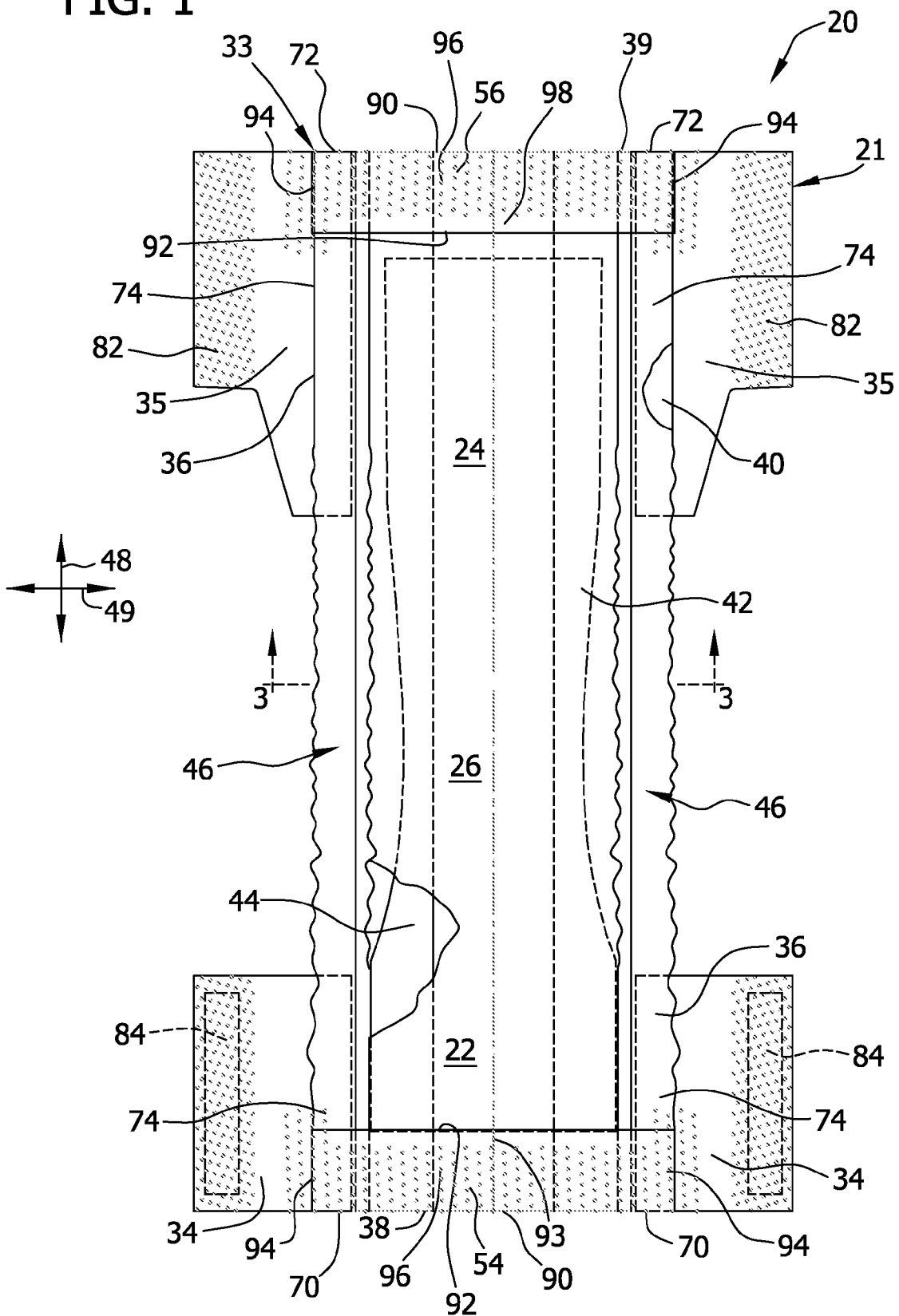
FIG. 1 is a top plan view of one embodiment of an absorbent article in the form of a training pant being in an unfastened, unfolded and laid flat condition, and showing the surface of the training pant that faces a wearer during use.

With reference now to the drawings, and in particular to FIG. 1, an absorbent article in the form of a training pant is illustrated in an unfastened, unfolded and laid-flat condition and indicated generally by reference number 20. The training pant 20 comprises a chassis, indicated at 21, having a generally rectangular absorbent structure, indicated at 33, a pair of laterally opposite front side panels 34, and a pair of laterally opposite back side panels 35. For reference, arrows 48 and 49 depict the orientation of the longitudinal axis and the transverse or lateral axis, respectively, of the training pant 20. It is contemplated that the absorbent article can have other forms without departing from some aspects of this invention (e.g., a diaper and incontinence article).

The absorbent structure 33 of the training pant 20 is configured to contain and/or absorb exudates released by a wearer of the training pant. As seen in FIG. 1, the absorbent structure 33 has a front waist region 22, a back waist region 24, and a crotch region 26 extending between and interconnecting the front and back waist regions. The absorbent structure 33 further includes a pair of side edges 36, a front waist edge 38, and back waist edge 39. The absorbent structure 33 and side panels 34, 35 may comprise separate elements, as shown in FIG. 1, or be integrally formed.

The illustrated absorbent structure 33 comprises an outer cover 40, a body-side liner 42, and an absorbent assembly 44 disposed between the outer cover and the body-side liner. In one suitable embodiment, the outer cover 40 comprises a material that is substantially liquid impermeable, and can be elastic, stretchable, or nonstretchable. The outer cover 40 can be a single layer of liquid impermeable material, but suitably comprises a multi-layered laminate structure in which at least one of the layers is liquid impermeable. For instance, the outer cover 40 can include a liquid permeable outer layer and a liquid impermeable inner layer that are joined together by a laminate adhesive, ultrasonic bonds, thermal bonds, or the like. Suitable laminate adhesives can be applied continuously or intermittently as beads, a spray, parallel swirls, or the like. The liquid permeable outer layer can be any suitable material and desirably one that provides a generally cloth-like texture. The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, inhibits liquid exudates from wetting articles, such as bed sheets and clothing, as well as the wearer and caregiver.

The body-side liner 42 is liquid permeable and overlies the absorbent assembly 44 and outer cover 40. In one suitable embodiment, a width of the body-side liner 42 is less than the width of the outer cover 40. In the illustrated embodiment, for example, the outer cover 40 has a width of approximately 169 millimeters and the body-side liner has a width of approximately 130 millimeters. Thus, longitudinal side portions of the outer cover 40 are uncovered by the body-side liner. In the illustrated embodiment, each of the longitudinal side portions of the outer cover 40 have a width of approximately 19.5 millimeters. It is understood, however, that the body-side liner 42 and the outer cover 40 dimensions other than those illustrated herein. For example, the body-side liner 42 and the outer cover 40 can have substantially the same dimension or the liner 42 can be wider than the outer cover 40.

The body-side liner 42 suitably presents a bodyfacing surface of the training pant 20, which is compliant, soft feeling, and non-irritating to the wearer's skin. Further, the body-side liner 42 may be less hydrophilic than the absorbent assembly 44, to present a relatively dry surface to the wearer, and may be sufficiently porous to be liquid permeable, permitting liquid to readily penetrate through its thickness. A suitable body-side liner 42 may be manufactured from a wide selection of web materials, such as porous foams, reticulated foams, apertured plastic films, natural fibers (i.e., wood or cotton fibers), synthetic fibers (i.e., polyester or polypropylene fibers), or a combination of natural and synthetic fibers. The body-side liner 42 is suitably employed to help isolate the wearer's skin from liquids held in the absorbent assembly 44.

The body-side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body-side liner 42. For example, the body-side liner 42 can be composed of a meltblown or spunbonded web of polyolefin fibers. The body-side liner can also be a bonded-carded web composed of natural and/or synthetic fibers. The body-side liner can be composed of a substantially hydrophobic material, and the hydrophobic material can, optionally, be treated with a surfactant or otherwise processed to impart a desired level of wettability and hydrophilicity. In one suitable embodiment, for example, the body-side liner 42 can be a hydrophobic three-layer nonwoven polypropylene material known as SMS. SMS is an acronym for Spunbond, Meltblown, Spunbond, the process by which the three layers are constructed and then laminated together. One example of an SMS material is described in U.S. Pat. No. 4,041,203 to Brock et al.

The absorbent assembly 44 is generally compressible, conformable, non-irritating to the wearer's skin, and capable of absorbing and retaining liquids and certain body wastes, and may be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Typically, a superabsorbent material is capable of absorbing at least about 15 times its weight in water, and desirably is capable of absorbing more than about 25 times its weight in water. As a general rule, the superabsorbent material is present in the absorbent assembly 44 in an amount of from 0 to about 90 percent weight based on total weight of the absorbent assembly. The absorbent assembly 44 may or may not be wrapped or encompassed by a suitable tissue wrap that may help maintain the integrity and/or shape of the absorbent assembly.

In the illustrated embodiment, a width of the absorbent assembly 44 varies along its length to provide a more comfortable fit to the wearer. More specially, the illustrated absorbent assembly 44 has a width of approximately 115 millimeters in the front waist region 22 of the absorbent structure 33 and approximately 101 millimeters in the back waist region 24 of the absorbent structure. The width of the absorbent assembly tapers inward along its length from the front waist region 22 and the back waist region 24 towards the crotch region 26 to a minimum width of the absorbent assembly 44. The minimum width of the illustrated absorbent assembly 44, which is the crotch region of the absorbent structure 33 is approximately 85 millimeters. It is understood that the absorbent assembly 44 can have any suitable shape and size.

The absorbent structure 33 can also incorporate other materials designed primarily to receive, temporarily store, and/or transport liquid along the mutually facing surface with absorbent assembly 44, thereby maximizing the absorbent capacity of the absorbent assembly. One suitable material is referred to as a surge management layer (not shown) and may be located adjacent the absorbent assembly 44 (e.g., between the absorbent assembly and the liner 42). The surge management layer helps to decelerate and diffuse surges or gushes of liquid that may be rapidly introduced into the absorbent assembly 44. The surge management layer can rapidly accept and temporarily hold the liquid prior to releasing the liquid into the storage or retention portions of the absorbent assembly 44. Examples of suitable surge management layers are described in U.S. Pat. Nos. 5,486,166 and 5,490,846. Other suitable surge management materials are described in U.S. Pat. No. 5,820,973.

As seen in FIG. 1, the front and back side panels 34, 35 are disposed on laterally opposite sides of the absorbent structure 33 in longitudinally spaced relationship with each other. In the illustrated embodiment, the front and back side panels 34, 35 are permanently bonded along seams to the absorbent structure 33 in the respective front and back waist regions 22, 24. More specifically, each of the front and back side panels 34, 35 are sandwiched between the outer cover 40 and the body-side liner 44 permanently bonded to both the outer cover and the body-side liner. The front side panels 34 extend transversely outward beyond the side edges 36 of the absorbent structure 33 in the front waist region 22, and the back side panels 35 extend transversely outward beyond the side edges of the absorbent structure in the back waist region 24.

The front and back side panels 34, 35 may be bonded to the absorbent structure 33 using attachment means known to those skilled in the art such as adhesive, thermal or ultrasonic bonding. In the illustrated embodiment, for example, the front and back side panels 34, 35 are adhesively bonded to both the outer cover 40 and the body-side liner 44.

As mentioned above, the front and back side panels 34, 35 can be formed as an integral portion of a component of the absorbent structure 33. For example, the front and back side panels can comprise a generally wider portion of the outer cover 40 and/or the body-side liner 42.

In one suitable embodiment, the front and back side panels 34, 35 comprise an elastic material capable of stretching in a direction generally parallel to the transverse axis 49 of the training pant 20. Suitable elastic materials, as well as one process of incorporating elastic side panels into training pant, are described in U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.

In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al. Alternatively, the side panel material may comprise other woven or nonwoven materials, such as those described above as being suitable for the outer cover 40 or body-side liner 42, mechanically prestrained composites, or stretchable but inelastic materials.

The illustrated training pant 20 includes a fastening system 80 for refastenably securing the training pant about a waist of the wearer. It is understood, however, that the front and back side panels 34, 35 can be permanently bonded together. The illustrated fastening system 80 includes first fastening components 84 adapted for refastenable engagement to corresponding second fastening components 82. In the illustrated embodiment, the first fastening components 84 comprise a plurality of projecting engaging elements. The engaging elements of the first fastening components 84 are adapted to repeatedly engage and disengage engaging elements of the second fastening components 82.

The fastening components 84, 82 can comprise separate elements bonded to the side panels 34, 35, or they may be integrally formed with the side panels. In the illustrated embodiment, for example, the first fastening components 84 are formed separate from the front side panels 34 and bonded thereto. The second fastening components 82, on the other hand, are integrally formed with the back side panels 35. The first fastening components 84 can be bonded to the respective front side panels 34 by any means known to those skilled in the art such as adhesive bonds, ultrasonic bonds or thermal bonds.

The fastening components 84, 82 can comprise any refastenable fasteners suitable for absorbent articles, such as adhesive fasteners, cohesive fasteners, mechanical fasteners, or the like. In the illustrated embodiment, the fastening components 84, 82 comprise mechanical fastening elements. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 84 comprise hook fasteners and the second fastening components 82 comprise complementary loop fasteners. In another suitable embodiment, the first fastening components 84 comprise loop fasteners and the second fastening components 82 comprise complementary hook fasteners. Alternatively, the fastening components 84, 82 may comprise interlocking similar surface fasteners, adhesive or cohesive fastening elements such as an adhesive fastener and an adhesive-receptive landing zone or material; or the like.

Figure 2:
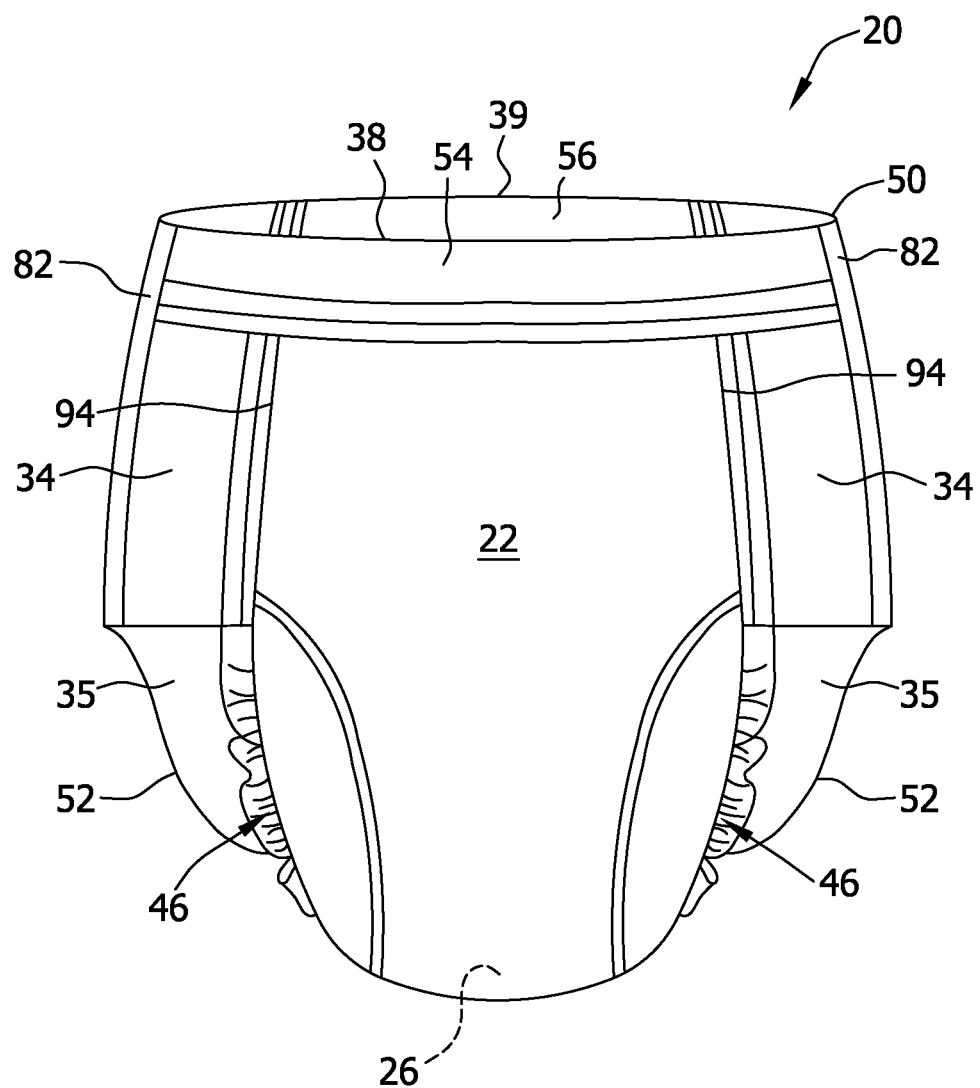
FIG. 2 is a front perspective of the training pant of FIG. 1 having a mechanical fastening system fastened to define a wear configuration of the training pant.

In a ready-to-wear, three dimensional configuration of the training pant 20, which is illustrated in FIG. 2, the front and back side panels 34, 35 are secured together to define a three-dimensional pants configuration having a waist opening 50 and a pair of leg openings 52. The front waist region 22 comprises the portion of the training pants which, when worn, is positioned on the front of the wearer while the back waist region 24 comprises the portion of the training pants which, when worn, is positioned on the back of the wearer. The crotch region 26 of the training pant 20 comprises the portion of the training pants which, when worn, is positioned between the legs of the wearer and covers the lower torso of the wearer. The front and back side panels 34, 35 define the portions of the training pant 20 which, when worn, are positioned on the hips of the wearer. The waist edges 38, 39 of the absorbent chassis 21 are configured to encircle the waist of the wearer when worn and together define the waist opening 50.

As seen in FIG. 2, in the ready-to-wear, three dimensional configuration of the training pant 20, the back side panels 35 overlaps the front side panels 34 when the first fastening component 84 is engaged with the second fastening component 82. It is understood, however, that the training pant 20 may instead be configured so that the front side panels 34 overlap the back side panels 35.

Figure 3:
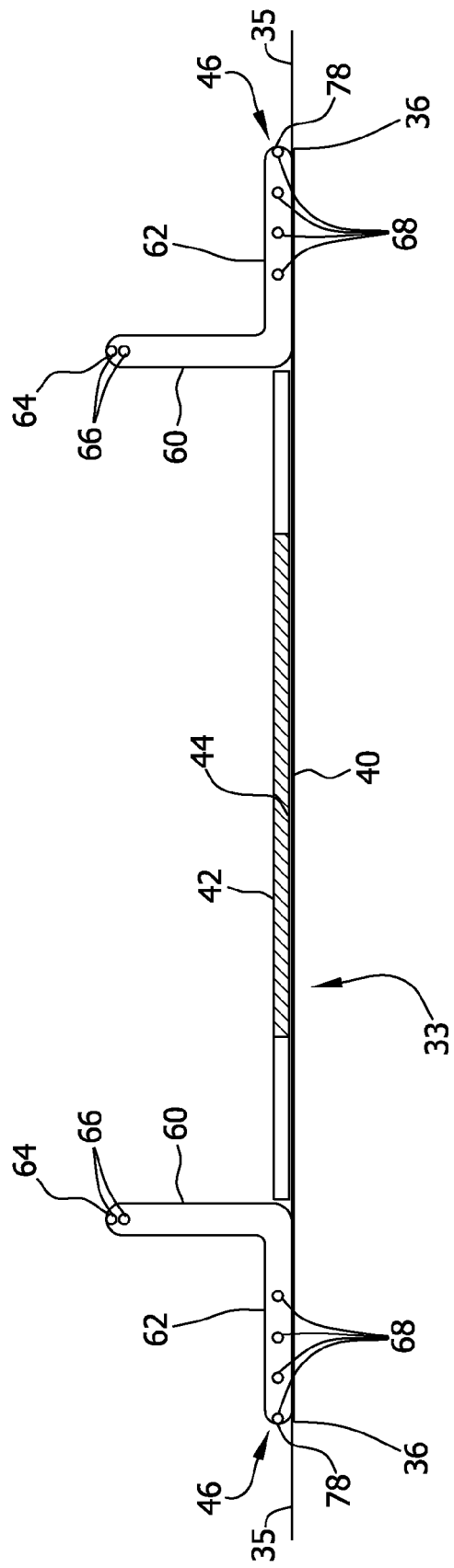
FIG. 3 is a cross-section of the training pant taken along line 3-3 of FIG. 1.

With reference now to FIGS. 1 and 3, each of the leg and flap elastic composites 46 has a containment flap portion 60 and a gasket portion 62. In the illustrated embodiment, the leg and flap elastic composites 46 extend longitudinally along the entire length of the absorbent structure 33. It is contemplated that the leg and flap elastic composites 46 can extend less than the entire length of the absorbent chassis 33. It is also contemplated that one of the containment flap portion 60 or the gasket portion 62 can extend less than the entire length of the absorbent chassis 33.

The containment flap portion 60 of each of the leg and flap elastic composites 46 provides a barrier to the transverse flow of body exudates released by the wearer. More specifically, each of the containment flap portions 60 assumes an upright configuration during use to define an unattached edge 64 in at least the crotch region 26 of the absorbent structure 33 of the training pant 20 to form a seal against the wearer's body. In the illustrated embodiment, the containment flap portions 60 of the leg and flap elastic composites 46 are generally aligned with lateral side edges of the absorbent assembly 44 in at least the crotch region of the absorbent structure 33. It is contemplated that the containment flap portions 60 can be spaced inward or outward from the respective lateral side edge of the absorbent assembly 44.

The containment flap portions 60 of the illustrated embodiment lie generally flat in at least a portion of the front waist region 22 and the back wait region 24 of the absorbent structure 33 during use of the training pant 20. Thus, in the front and back waist regions 22, 24 of the absorbent structure 33, the containment flap portions 60 lie in generally face-to-face relationship with the body-side liner 42.

As seen in FIG. 3, each of the containment flap portions 60 of the leg and flap elastic composites 46 comprises two elastic members 66 operatively joined thereto. In the illustrated embodiment, the elastic members 66 are adhesively bonded to the containment flap portions 60 of the leg and flap elastic composites 46 but it is understood that the elastic members can be operatively joined to the leg and flap elastic composite in any suitable manner as is well known in the art. It is also understood that the leg and flap elastic composites 46 can include more or fewer elastic members 66 and that the elastic members can be any suitable elastomeric material (e.g., strands, ribbons). In the illustrated embodiment, for example, the elastic members 66 are elastic strands having a decitex of about 800.

The gasket portions 62 of the leg and flap elastic composites 46 seal against the legs of the wearer when the wearer's legs are received in the leg openings 52 of the training pant 20.

In the illustrated embodiment, the gasket portions 62 are generally aligned with the side edges 36 of the absorbent structure 33 (which is defined by the outer cover 40) and extend longitudinally along the entire length of the absorbent structure. It is contemplated, however, that the gasket portions 62 can be spaced inward or outward from the respective side edge 36 of the absorbent structure 33. It is also contemplated that the gasket portions 62 can extend less than the entire length of the absorbent chassis 33.

As seen in FIG. 3, each of the gasket portions 62 of the leg and flap elastic composites 46 comprises four elastic members 68 operatively joined thereto. In the illustrated embodiment, the elastic members 68 are adhesively bonded to the gasket portions 62 of the leg and flap elastic composites 64 but it is understood that the elastic members can be operatively joined to the leg and flap elastic composite in any suitable manner as is well known in the art. It is also understood that the gasket portions 62 of the leg and flap elastic composites 46 can include more or fewer elastic members 68 and that the elastic members can be made of any suitable elastomeric materials (e.g., strands, ribbons). In the illustrated embodiment, for example, the elastic members 68 are elastic strands having a decitex of about 470.

The gasket portions 62 of the leg and flap elastic composites 46 form a gasket (i.e., sealingly engage) with each the legs of the wearer when the wearer's legs are received through the respective leg openings 52. In addition, the gasket portions 62 extend into operative engagement with the respective front and back side panels 34, 35, which create fully encircling leg gaskets, which significantly inhibit leakage.

The presence or noticeability of the gasket portions 62 of the leg and flap elastic composites 46 can be enhanced by providing graphics and/or texturing (not shown) on the gasket portions. In one suitable embodiment, the graphics and/or texturing is provided to increase the noticeability of the fully encircling leg gaskets formed by the gasket portions 62.

The elastic members 66, 68 of the leg and flap elastic composites 46 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate.

As seen in FIG. 1, each of the leg and flap elastic composites 46 has a front edge 70 and a back edge 72. In the illustrated embodiment, the front edge 70 is generally coterminous with the front waist edge 38 of the absorbent structure 33 and the back waist edge 39 is generally coterminous with the back waist edge. It is contemplated, however, that the front and back edges 70, 72 of the leg and flap elastic composites 46 can be spaced inward from the respective front and back waist edges 38, 39 of the absorbent structure 33.

Each of the leg and flap elastic composites 46 include deadened portions 74 adjacent to both the front edge 70 and back edge 72 thereof. The deadened portions 74 are portions of the leg and flap elastic composites 46 wherein the elastic members 66 of the containment flap portions 60 and the elastic members 68 of the gasket portions 62 have been rendered inelastic. As seen in FIG. 1, the deadened portions 74 of the leg and flap elastic composites located in the back waist region 24 of the absorbent structure 33 extend further from the base waist edge 39 than do the deadened portions located in the front waist region 22 of the absorbent structure. In other words, the deadened portions 74 are longer in the back waist region 24 than they are in the front waist region 22. It is understood, however, that the deadened portion in the front waist region 22 can have the same length as the deadened portions in the back waist region 24. It is also understood that the deadened portion in the front waist region 22 can be longer than the deadened portions in the back waist region 24.

In one suitable embodiment, outer side edges 78 of each of the leg and flap elastic composites 46, which are defined by the gasket portions 62, are aligned with the respective side edge 36 of the outer cover 40. In other words, the outer side edges 78 of the leg and flap elastic composites 46 and the side edges 36 of the outer cover 40 are coterminous (FIG. 3). This configuration creates a cuff-like appearance at the leg opening 52 which can be perceives as being underwear-like. In another suitable embodiment, the outer side edges 78 of the leg and flap elastic composites 46 can extend outward beyond the respective sides edge 36 of the outer cover 40.

As seen in FIG. 1, the training pant includes a front waist elastic member 54, and a rear waist elastic member 56. The waist elastic members 54, 56 can be formed of any suitable elastic material. Suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate.

In the illustrated embodiment, both the front and back waist elastic members 54, 56 are generally rectangular in shape having a top edge 90, a bottom edge 92, and two side edges 94. The illustrated front and back waist elastic members 54, 56 have a length (i.e., the distance between the side edges 94) of about 170 millimeters and a width (i.e., the distance between the top edge 90 and the bottom edge 92) of about 38 millimeters. It is understood that the front waist elastic member 54 and/or the back waist elastic member 56 can be of other suitable shapes and sizes.

In one suitable embodiment and as seen in FIG. 1, the top edges 90 of the front and back waist elastic members 54, 56 are generally aligned with the front waist edge 38 and back waist edge 39, respectively, of the outer cover 40. It is understood that the top edges 90 of the front waist elastic member 54 and/or the back waist elastic member 56 can be spaced from the respective front waist edge 38 or the back waist edge 39.

In one suitable embodiment, the front and back waist elastic members 54, 56 are both adhesively bonded and point bonded to the absorbent structure 33. In the illustrated embodiment, for example, the front and back waist elastic members 54, 56 are adhesively bonded and point bonded to the inner surface of the absorbent structure 33 (i.e., the surface of the absorbent structure that faces the wearer during use of the training pant 20). More specifically, the front and back waist elastic members 54, 56 are adhesively bonded to the body-side liner 42 and the deadened portions 74 of the leg and flap elastic composites 46.

The front and back waist elastic members 54, 56 are also point bonded to the body-side liner 42, the outer cover 40, and the deadened portions 74 of the leg and flap elastic composites 46 via a plurality of point bonds 96. As seen in FIG. 1, the point bonds 96 extend up to the upper edges 90 and beyond the side edges 94 of the front and back waist elastic members 54, 56. That is, the point bonds 96 extend in the transverse direction of the absorbent structure 33 beyond the front and back waist elastic members 54, 56 and onto the respective front side panel 34 or back side panel 35.

As also seen in FIG. 1, the lower edges 92 of the front and back waist elastic members 54, 56 are point bonded to the deadened portions 74 of the leg and flap elastic composites 46. Thus, the side edges 94 of each of the front and back waist elastic members 54, 56 are point bonded along their entire lengths. In fact, the point bonds 96 extend beyond the lower edges 92 of the front and back waist elastic members 54, 56 adjacent the side edges 94.

Figure 8:
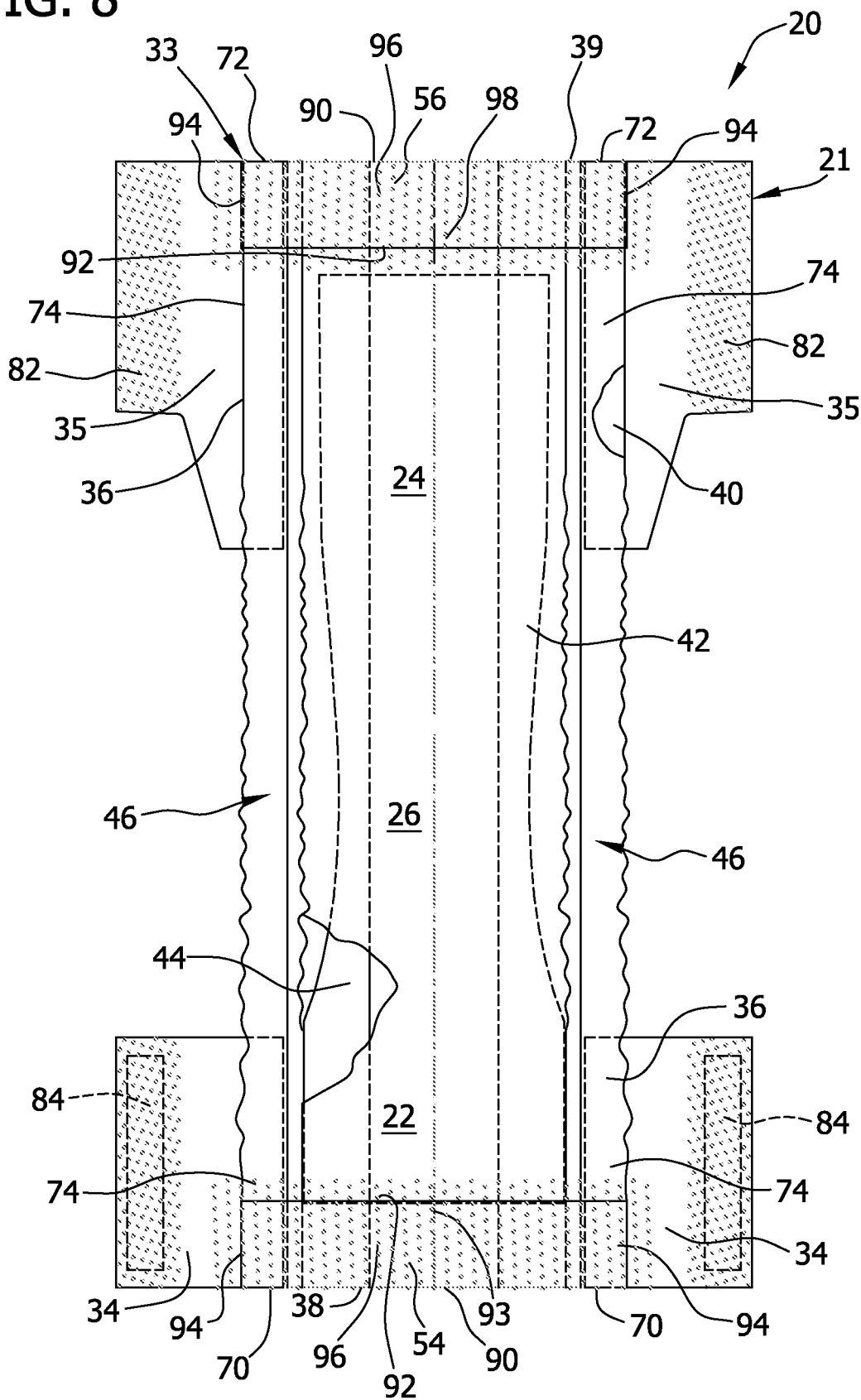
FIG. 8 is a top plan view of another embodiment of an absorbent article in the form of a training pant being in an unfastened, unfolded and laid flat condition, and showing the surface of the training pant that faces a wearer during use.

A lower, middle portion 98 of each of the front and back waist elastic members 54, 56 are free of point bonds 96. In the illustrated embodiment, the lower, middle portion 98 has a width of approximately 7 millimeters and a length of approximately 154 millimeters. It is understood, however, that the width and length of the non-point bonded lower, middle portion can differ. As a result, a significant portion of the lower edges 92 of the front and back waist elastic members 54, 56 are not point bonded. It is also contemplated that the lower, middle portion 98 of each of the front and back waist elastic members 54, 56 can be point bonded 96 as illustrated in FIG. 8.

As seen in FIG. 1, the point bonds 96 are generally aligned in longitudinally extending rows with each of the rows being generally uniformly spaced apart, which provides uniform gathers in the front and back waist elastic members 54, 56. In one suitable embodiment, the spacing between the rows can be within a range between about 3 millimeters and about 12 millimeters. In the illustrated embodiment, for example, the spacing between the longitudinally extending rows of point bonds 96 is about 5 millimeters. It is understood that the spacing between the longitudinally extending rows can differ.

In one suitable embodiment, the spacing between the point bonds 96 within the longitudinal extending rows is less than about 10 millimeters. For example, the spacing between point bonds 96 within the longitudinal extending rows in the illustrated embodiment is about 5 millimeters. It is understood that the spacing between point bonds 96 within the longitudinally extending rows can differ.

As seen in FIG. 1, the illustrated bond points 96 are generally circular and have a diameter of less than about 10 millimeters and suitably, between about 0.5 millimeters and about 3 millimeters. In the illustrated embodiment, for example, the bond points 96 have a diameter of approximately 1 millimeter. It is understood, however, that the bond points can have any suitable size or shape. For example, the diameter of the point bonds 96 can be between approximately 0.5 millimeters and about 10 millimeters.

In the illustrated embodiment, the front waist elastic member 54 is bonded to the absorbent structure 33 in substantially the same manner as the back waist elastic member 56. It is contemplated, however, that the front waist elastic member 54 and back waist elastic member 56 can be bonded to the absorbent structure 33 in different manners. It is also contemplated that the front waist elastic member 54 and/or the back waist elastic member 56 can be bonded to the absorbent structure 33 using one of adhesive bonding or point bonding.

Figure 4:
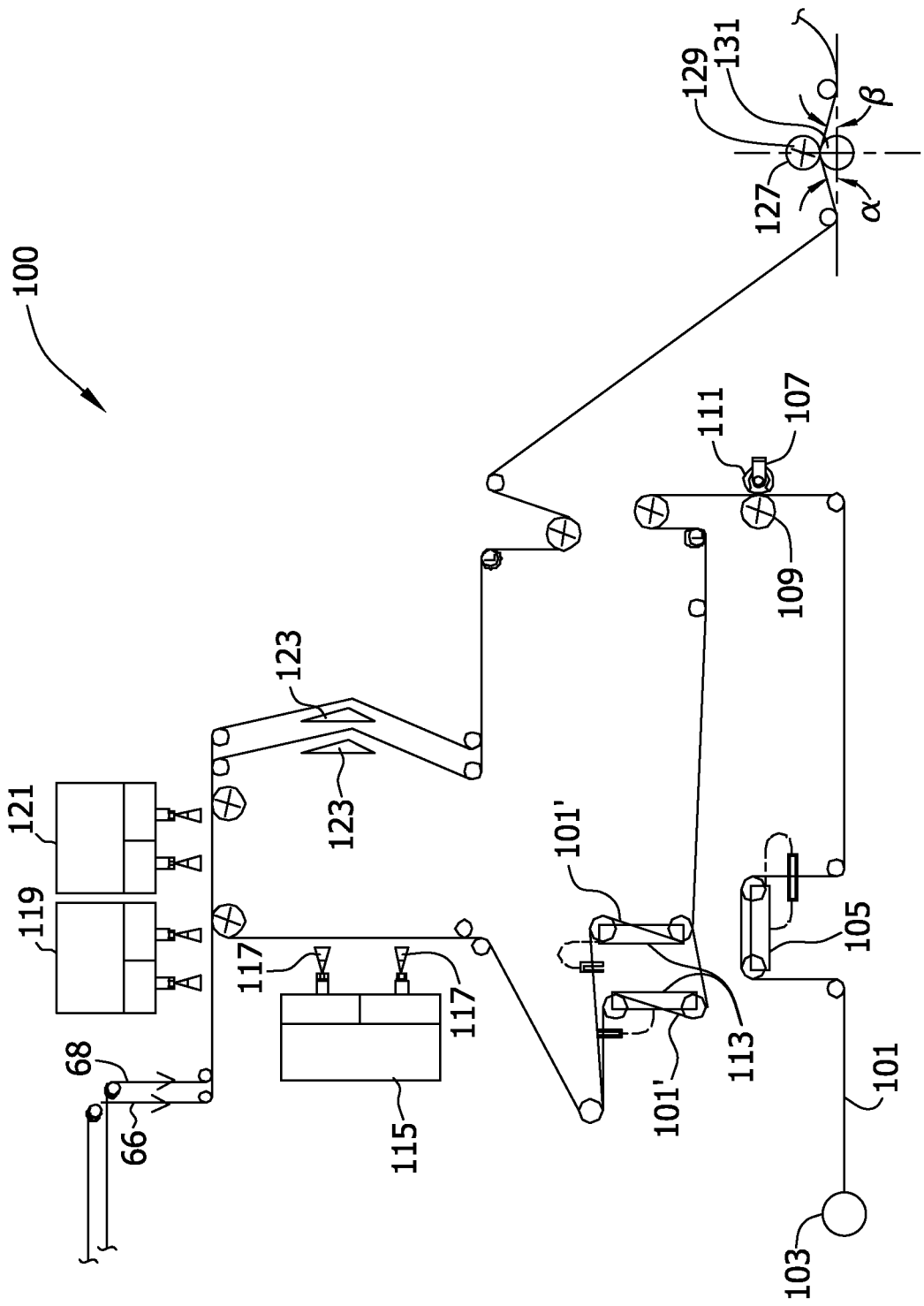
FIG. 4 is a schematic illustrating one suitable apparatus for manufacturing leg and flap elastic composites for use in the training pant of FIGS. 1-3.
Figure 5D:
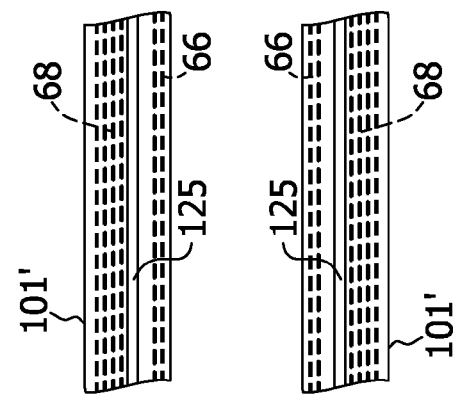
FIGS. 5A-5D are top plan views of a web, a leg elastic member, and a flap elastic member at various stages along the apparatus of FIG. 4.

FIG. 4 schematically illustrates one suitable apparatus 100 for manufacturing the leg and flap elastic composites 46. As seen therein, a continuous web 101 of SMS (or other suitable material) having a width W is fed from a supply roll 103 through a first web guide 105 to a slitter assembly 107. A cut-away portion of the web 101 being fed to the slitter assembly 107 is illustrated in FIG. 5A. The illustrated slitter assembly 107 comprises an anvil roll 109 and slitting blade 111 for cutting the web 101 generally in half in the machine direction (i.e., along a longitudinal centerline CL of the web (FIG. 5A)) to form two longitudinal segments 101' of the web 101. Each of the web segments 101' have generally the same width W/2, which is about half the width W of the pre-cut web 101 (FIG. 5B). It is understood that the slitter assembly 107 can be omitted and that the web segments 101' can be fed from discrete supply rolls.

As seen in FIG. 4, each of the web segments 101' are fed past a second web guide 113 to an adhesive applicator 115 which applies a suitable adhesive 117 to one side of each web segment 101'. Next, leg elastic members 68 and flap elastic members 66 are applied to each of the web segments 101' such that the leg and flap elastics 68, 66 are bonded to the respective segment by the adhesive 117. As seen in FIG. 4, the leg elastic members 68 are adhesively bonded to each of the web segments 101' at a leg elastic attachment station 119, and the flap elastic members 66 are adhesively bonded to each of the web segments at a flap elastic attachment station 121.

Figure 5C:
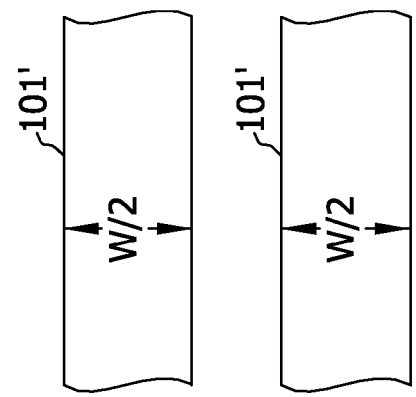
Figure 5B:
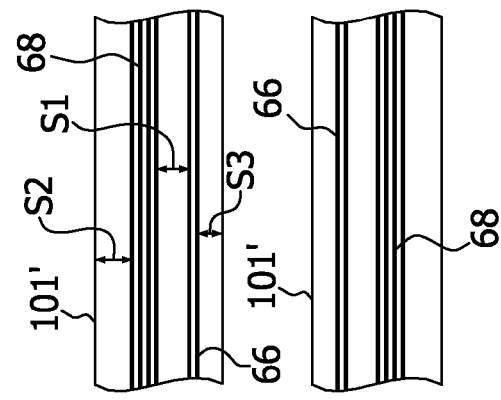
Figure 5A:
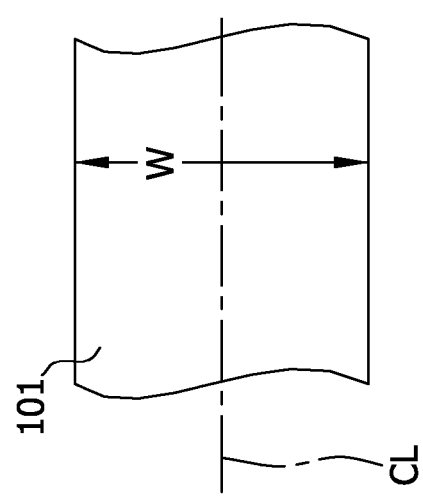

With reference now to FIG. 5C, the leg elastic members 68 are spaced from the flap elastics 66 to define a first spacing S1. In addition, each of the leg elastic members 68 are spaced inward from a longitudinal edge of each of the respective web segments 101' by a second spacing S2, and each of the flap elastic members 66 are spaced inward from an opposite longitudinal edge of each of the respective web segments by a third spacing S3.

In the illustrated embodiment, the leg elastic members 68 comprise four elastic strands and the flap elastic members 66 comprise two elastic strands. The strands of leg elastic members 68 and the strands of the flap elastic members 66 are spaced about 5 millimeters from each other but it is understood that the spacing between adjacent strands can be different. As mentioned above, any suitable elastomeric material (e.g., ribbons) can be used as the leg and flap elastic members 68, 68.

With reference again to FIG. 4, each of the web segments 101' is fed to a respective folding board 123 where the longitudinal side edges of the segments are folded inward such that the respective web segment encloses the leg and flap elastic members 68, 68. The side edges of the respective segments 101' are overlapped and adhesive bonded together to define an engagement seam 125 at a location between the leg and flap elastic members 68, 66 (FIG. 5D). In other words, the engagement seam 125 is formed in the first spacing S1 between the leg and flap elastic members 68, 66.

The folded web segments 101' are then fed to a chopper assembly 127 where portions of the leg and flap elastic members 68, 66 are deadened to define the deadened portions 74 of the leg and flap elastic composites 46. As illustrated in FIG. 4, the chopper assembly 127 includes a knife roll 129 and an anvil roll 131 for operatively dividing portions of each of the strands defining the leg elastic members 68 and the flap elastic members 66 into a plurality of pieces to effectively render the deadened portions 74 of each leg and flap elastics composite 46 non-elastomeric. The chopper assembly 127 may include any operative dividing device, such as a cutting device, a heating device, an ultrasonic device, or the like as well as combinations thereof.

The web segments 101' enter the chopper assembly 127 at an approach angle $\alpha$ greater than approximately 20 degrees and exits the chopper assembly at an exit angle $\beta$, which is also greater than approximately 20 degrees. In the illustrated embodiment, for example, the approach angle $\alpha$ and the exit angle $\beta$ are both approximately 30 degrees. The approach angle $\alpha$ and the exit angle $\beta$ are predetermined to facilitate the web segments 101' passing through the chopper assembly 127 in proper alignment. More specifically, the strands 66, 68 of the web segments 101' would rapidly snap back upon being cut by the chopper assembly 127 forming "balls" or "tangles" if not controlled. The strands 66, 68, however, can be controlled by setting the approach angle α and exit angle β greater than approximately 20 degrees and using idler rolls near the entry and exit of the chopper assembly 127 to control the retraction of the strands 66, 68 upon their cutting (FIG. 4). It is contemplated that the approach angle α and the exit angle β can be different than those illustrated herein. It is further contemplated that the approach angle α and the exit angle β can differ from each other.

Figure 6:
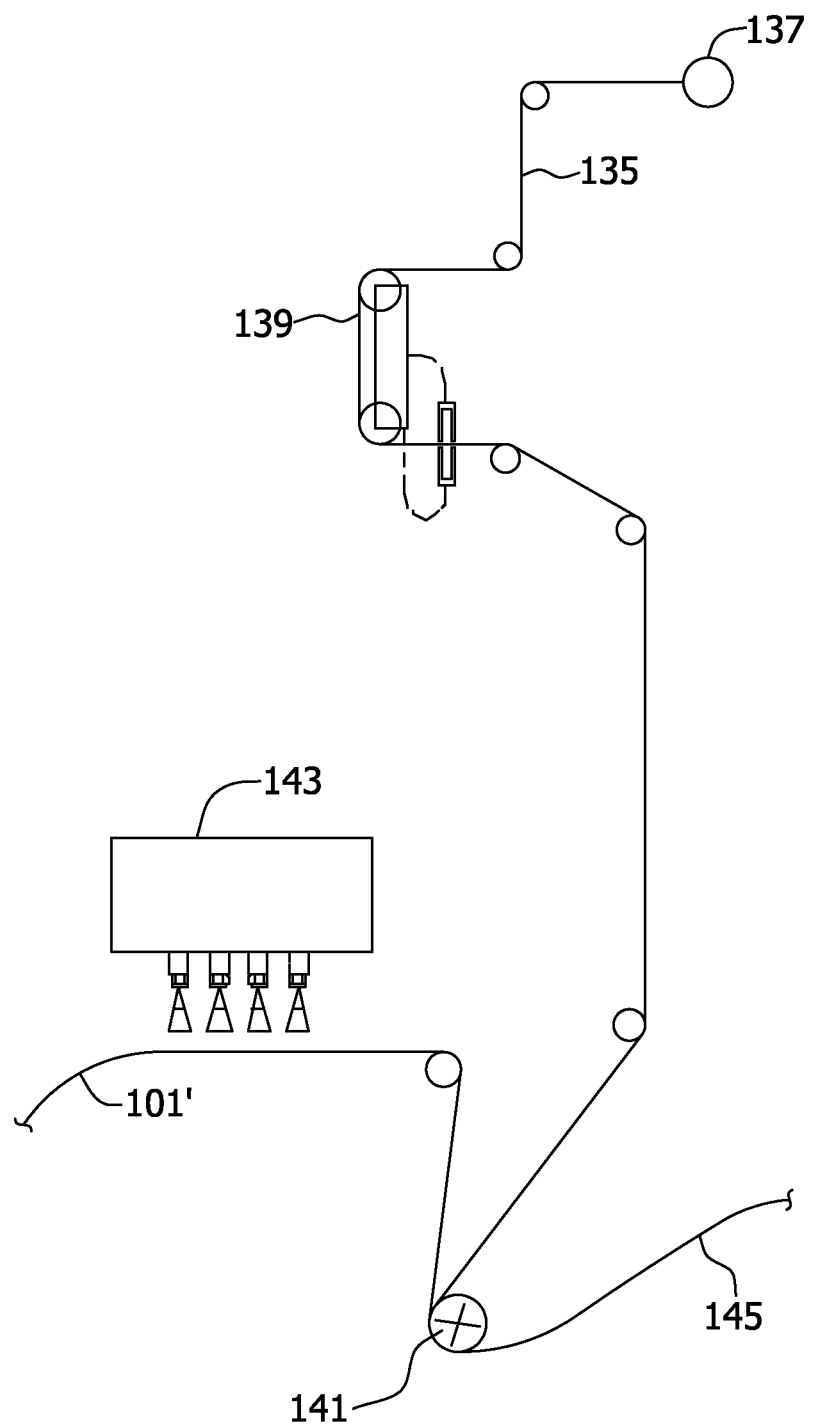
FIG. 6 is a schematic illustrating one suitable apparatus for bonding the leg and flap elastic composites to a web of body-side liner material to form a liner/composite web.

FIG. 6 schematically illustrates the web segments 101' being bonded to a web of body-side liner material 135 (broadly, "a substrate"). In the illustrated embodiment, the web of suitable body-side liner material 135 is fed from a continuous roll 137 past a liner in-feed web guide 139 to a bonder 141 where the web segments 101' that define the leg and flap elastic composites 46 are adhesively bonded to the web of body-side liner material 135 adjacent respective side edges. As seen in FIG. 6, the web segments 101' are fed past an adhesive applicator 143 prior to being adhesively bonded to the web of body-side liner material 135. It is understood, however, that the web segments 101' can be bonded to web of body-side liner material using any suitable bonding technique.

Figure 7:
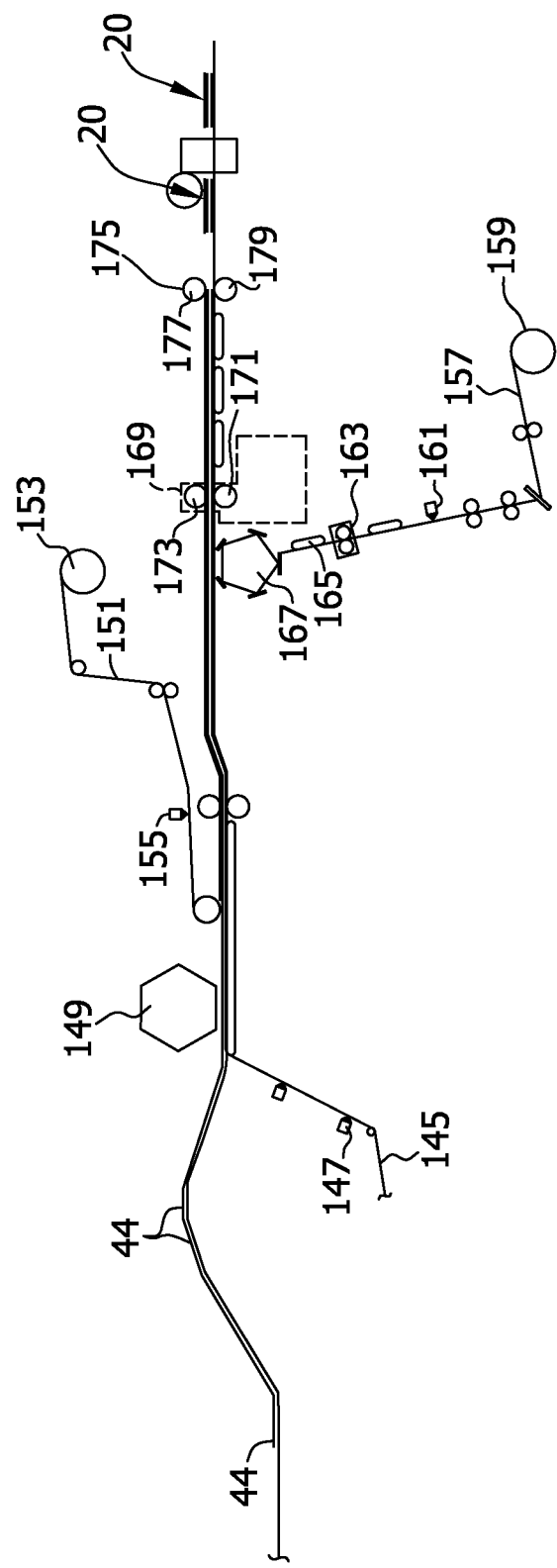
FIG. 7 is a schematic illustrating one suitable apparatus for manufacturing training pants using the liner/composite web of FIG. 6.

FIG. 7 schematically illustrates the web of body-side liner material 135 having the web segments 101' (collectively, a "liner/composite web 145") bonded thereto being used to manufacture training pants, such as the training pant 20 illustrated in FIGS. 1 and 2. The liner/composite web 145 is fed in a machine direction past an adhesive applicator 147 with the web segments 101' facing downward wherein adhesive is applied to the liner/composite web. As seen in FIG. 7, a plurality of discrete absorbent assemblies 44 are fed to and adhesively bonded by the adhesive to the liner/composite web 145 on its side opposite the leg and flap elastic composites 46.

After the absorbent assemblies are adhesively bonded to the liner/composite web 145, the front and back side panels 34, 35 are then attached at spaced intervals to respective side edges of the liner/composite web 145 at side panel application station 149. The side panels 34, 35 can be supplied and attached to the liner/composite web 145 in any suitable manner.

Next a web of outer cover material 151 is bonded to the liner/composite web 145. More specifically, the web of outer cover material 151 is fed from a supply roll 153 past an adhesive applicator 155, which applies adhesive thereto. The web of outer cover material 151 is adhesively bonded to the liner/composite web 145 so that the web of outer cover material sandwiches the absorbent assemblies 144 and portions of each of the front and back side panels 34, 35 between the liner/composite web and the web of outer cover material.

The front and back waist elastic members 54, 56 are then bonded to the liner/composite web 145 opposite the web of outer cover material 151. More specifically, the front and back waist elastic members 54, 56 are adhesively bonded and point bonded to the web of body-side liner material 131 and the web segments 101'. As seen in FIG. 7, a web of elastomeric material 157 is unwound from a supply roll 159 and fed past an adhesive applicator 161, which applies adhesive to the web of elastomeric material. The web of elastomeric material 157 is then cut into discrete elastic members 165 at a cutting station 163.

As explained in more detail below, each of the discrete elastic members 165 will define the back waist elastic member 56 of a leading training pant 20 and the front waist elastic members 54 of an adjacent trailing training pant 20. Thus, the discrete elastic members 165 have a width that is approximately twice the width of both the front waist elastic member 54 and the back waist elastic member 56. In the illustrated embodiment, for example, the discrete elastic members 165 have a width of approximately 76 millimeters, which is twice the 38 millimeter width of the illustrated front and back waist elastic members 54, 56.

The discrete elastic members 165 are adhered to the liner/composite web 145 by a waist elastic applicator 167 at spaced intervals directly to the web of body-side liner material 135 and the web segments 101'. In one suitable embodiment, the side edges of the discrete elastic members 165 generally align with the side edge of the liner/composite web 145.

After being adhesively bonded to the liner/composite web 145, the discrete elastic members 165 are then point bonded to the liner/composite web 145 at a point bonding station 169. In the illustrated embodiment, the point bonding station 169 includes a pattern roll 171 and an anvil roll 173 configured to point bond the elastic members 165 to the liner/composite web 145 in a pattern. In one suitable embodiment, the pattern roll 171 is heated and includes a plurality of raised landing portions. The raised portions of the pattern roll 171 thermally bond the discrete elastic members 165 to the web of body-side liner material 135 and the web segments 101'. In one suitable embodiment, the raised landing portions of the pattern roll 171 are generally aligned in an I-shape, with the "I" being aligned transversely across the pattern roll 171. The point bonds created by the point bonding station 169 also bond the liner/composite web 145 to the web of outer cover material 151. In another suitable embodiment, the raised landing portions of the pattern roll 171 can be generally aligned to form a rectangle, which forms the point bond pattern illustrated in FIG. 8.

The point bonds 96, which are illustrated in FIGS. 1 and 8, created by the point bonding station 169 can made of any suitable shape and size. In the illustrated embodiment, for example, the point bonds 96 are generally circular and have a diameter of about 1 millimeter.

In the illustrated embodiment, the elastic members 165 are activated by heat retraction, which causes the elastic members to gather. The gathering of the elastic members 165 is controlled by the point bonds 96, which are generally arranged in longitudinally extending columns. More specifically, the material of the elastic members 165 between the columns formed by the point bonds 96 gathers creating a uniform gathered appearance at the waist of the training pant 20. Moreover, fully bonding the front and back waist elastic members 54, 56 eliminates tunnels thus reducing the potential for leakage through the ends of the training pant 20. Furthermore, extending the point bonds 96 beyond the side edges 94 of the front and back waist elastic members 54, 56 ensures the waistband material is tacked down thus preventing the side edges of the front and back waist elastic members 54, 56 from curling.

A cutter assembly 175 then divides the web into discrete training pants (e.g., the training pant illustrated in FIGS. 1 and 2). In the illustrated embodiment, the cutter assembly 175 comprises a knife roll 177 and an anvil roll 179 that is configured to cut the web such that it divides each of the discrete elastic members 165 generally in half to define the back waist edge 39 of the leading training pant 20 and the front waist edge 38 of the trailing training pant.

Downstream from the cutter assembly 175, the front and back side panels 34, 35 of the training pant 20 can be connected, the training pant folded and packaged as is known in the art. It is contemplated that the above method of manufacture other types of absorbent articles besides training pants (e.g., diapers, incontinence articles).

When introducing elements of the present invention or the preferred embodiment(s) thereof, the articles "a", "an", "the"

and "said" are intended to mean that there are one or more of the elements. The terms "comprising", "including" and "having" are intended to be inclusive and mean that there may be additional elements other than the listed elements. Moreover, the use of "top", "bottom", "above", "below" and variations of these terms is made for convenience, and does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A method of manufacturing a leg and flap elastics composite for use in an absorbent article, the method comprising:
   joining a leg elastic member to a web moving in a machine direction;
   joining a flap elastic member to the web, the flap elastic member being spaced from the leg elastic member;
   feeding the web to a chopper assembly wherein portions of the leg and flap elastic members are rendered less elastic at spaced-apart intervals to define deadened portions of the leg and flap elastic members;
   folding the web such that the leg elastic member and the flap elastic member are enclosed by the web, wherein folding the web forms an outer side edge of the leg and flap elastics composite;
   attaching the leg and flap elastics composite to a web of outer cover material such that the outer side edge of the leg and flap elastics composite is coterminous with one of a pair of laterally opposing side edges of the web of outer cover material; and
   attaching an absorbent assembly to the web of outer cover material after the leg and flap elastics composite is attached to the web of outer cover material.

2. The method set forth in claim 1 wherein feeding the web to the chopper assembly comprises feeding the web between a knife roll and an anvil roll to divide portions of each of the leg elastic member and the flap elastic member into a plurality of pieces.

3. The method set forth in claim 1 wherein feeding the web to the chopper assembly comprises feeding the web at an approach angle that is greater than about 20 degrees.

4. The method set forth in claim 3 further comprising directing the web to exit the chopper assembly at an exit angle that is greater than about 20 degrees.

5. The method set forth in claim 1 wherein joining the leg elastic member to the web comprises adhesively bonding the leg elastic member to the web.

6. The method set forth in claim 5 wherein the leg elastic member comprises a plurality of elastomeric strands.

7. The method set forth in claim 1 wherein joining the flap elastic member to the web comprises adhesively bonding the flap elastic member to the web.

8. The method set forth in claim 7 wherein the flap elastic member comprises a plurality of elastomeric strands.

9. The method set forth in claim 1 further comprising cutting the web generally in half along a longitudinal centerline of the web to define a pair of web segments.

10. The method set forth in claim 1 wherein folding the web further comprises folding the web such that portions of the web are placed in overlapping relationship.

11. The method set forth in claim 10 further comprising bonding the overlapped portions of the web together.

12. A method of manufacturing an absorbent article having a leg and flap elastics composite, the method comprising:
    joining a leg elastic member to a web moving in a machine direction;
    joining a flap elastic member to the web to form the leg and flap elastics composite, the flap elastic member being spaced from the leg elastic member;
    feeding the leg and flap elastics composite to a chopper assembly wherein portions of the leg and flap elastic members are rendered less elastic at spaced-apart intervals to define deadened portions of the leg and flap elastic members;
    joining the leg and flap elastics composite to a substrate after the leg and flap elastics composite has been fed through the chopper assembly;
    aligning the web with the at least one edge of the substrate such that the web extends outward beyond the at least one edge;
    attaching a plurality of absorbent assemblies to the substrate;
    joining a web of outer cover material to the substrate such that an outer side edge of the leg and flap elastics composite is coterminous with one of a pair of laterally opposing side edges of the web of outer cover material; and
    cutting the substrate into a plurality of discrete absorbent articles.

13. The method set forth in claim 12 wherein the substrate is a body-side liner material and the method further comprises joining the web of outer cover material to the body-side liner material such that the outer cover material and the body-side liner material cooperatively sandwich the absorbent assemblies therebetween.

14. The method set forth in claim 12 further comprising joining a plurality of discrete waist elastic members to the substrate such that the waist elastic members are located within the deadened portions of the leg and flap elastic members.

15. The method set forth in claim 14 wherein joining the plurality of discrete waist elastic members to the substrate comprises point bonding the discrete waist elastic members to the substrate such that the bonding is within the deadened portions of the leg and flap elastic members.

16. The method set forth in claim 15 wherein point bonding the discrete waist elastic member to the substrate comprises directing the discrete waist elastic member and the substrate between a pattern roll and an anvil roll.

17. The method set forth in claim 16 wherein the pattern roll includes a plurality of raised landing portions having a generally rectangular pattern.

18. The method set forth in claim 14 wherein joining the plurality of discrete waist elastic members to the substrate comprises adhesively bonding and point bonding the discrete waist elastic members to the substrate.

19. The method set forth in claim 18 wherein cutting the substrate into a plurality of discrete absorbent articles comprises cutting the discrete waist elastic member to define waist elastic members on separate absorbent articles.

20. A method of manufacturing an absorbent article having a leg and flap elastics composite, the method comprising:
    joining a leg elastic member to a web moving in a machine direction;
    joining a flap elastic member to the web to form the leg and flap elastics composite, the flap elastic member being spaced from the leg elastic member;
    feeding the leg and flap elastics composite to a chopper assembly wherein portions of the leg and flap elastic members are rendered less elastic at spaced-apart intervals to define deadened portions of the leg and flap elastic members;

joining the leg and flap elastics composite to a substrate after the leg and flap elastics composite has been fed through the chopper assembly;

attaching a plurality of absorbent assemblies to the substrate after the leg and flap elastics composite is joined to the substrate;

joining a web of outer cover material to the substrate such that an outer side edge of the leg and flap elastics composite is coterminous with one of a pair of laterally opposing side edges of the web of outer cover material; and cutting the substrate into a plurality of discrete absorbent articles.

21. The method set forth in claim 20 wherein the substrate is a body-side liner material and the method further comprises joining the web of outer cover material to the body-side liner material such that the outer cover material and the body-side liner material cooperatively sandwich the absorbent assemblies therebetween.

22. The method set forth in claim 20 further comprising joining a plurality of discrete waist elastic members to the substrate such that the waist elastic members are located within the deadened portions of the leg and flap elastic members.

23. The method set forth in claim 22 wherein joining the plurality of discrete waist elastic members to the substrate comprises point bonding the discrete waist elastic members to the substrate such that the bonding is within the deadened portions of the leg and flap elastic members.

24. The method set forth in claim 22 wherein joining the plurality of discrete waist elastic members to the substrate comprises adhesively bonding and point bonding the discrete waist elastic members to the substrate.

25. The method set forth in claim 24 wherein cutting the substrate into a plurality of discrete absorbent articles comprises cutting the discrete waist elastic member to define waist elastic members on separate absorbent articles.

26. The method set forth in claim 23 wherein point bonding the discrete waist elastic member to the substrate comprises directing the discrete waist elastic member and the substrate between a pattern roll and an anvil roll.

27. The method set forth in claim 26 wherein the pattern roll includes a plurality of raised landing portions having a generally rectangular pattern.

28. The method set forth in claim 20 further comprising aligning the web flush with the at least one edge of the substrate.

* * * * *